(12) United States Patent
Mujwid et al.

(10) Patent No.: US 9,782,245 B2
(45) Date of Patent: Oct. 10, 2017

(54) IMPLANTS, TOOLS, AND METHODS FOR TREATMENT OF PELVIC CONDITIONS

(76) Inventors: James R. Mujwid, Edina, MN (US); John E. Titus, Lonsdale, MN (US)

( * ) Notice: Subject to any disclaimer, the term of this patent is extended or adjusted under 35 U.S.C. 154(b) by 418 days.

(21) Appl. No.: 14/008,170

(22) PCT Filed: Mar. 30, 2012

(86) PCT No.: PCT/US2012/031592
§ 371 (c)(1),
(2), (4) Date: Nov. 26, 2013

(87) PCT Pub. No.: WO2012/135710
PCT Pub. Date: Oct. 4, 2012

(65) Prior Publication Data
US 2014/0088344 A1    Mar. 27, 2014

Related U.S. Application Data

(60) Provisional application No. 61/469,458, filed on Mar. 30, 2011.

(51) Int. Cl.
*A61F 2/00*          (2006.01)
(52) U.S. Cl.
CPC .... *A61F 2/0045* (2013.01); *A61F 2250/0007* (2013.01)
(58) Field of Classification Search
CPC ...................... A61F 2250/0007; A61F 2/0045
USPC ..................................................... 600/29, 20
See application file for complete search history.

(56) References Cited

U.S. PATENT DOCUMENTS

| | | |
|---|---|---|
| 3,124,136 A | 3/1964 | Usher |
| 3,384,073 A | 5/1968 | Van Winkle, Jr. |
| 4,865,031 A | 9/1989 | O'Keeffe |
| 5,036,867 A | 8/1991 | Biswas |
| 5,112,344 A | 5/1992 | Petros |

(Continued)

FOREIGN PATENT DOCUMENTS

| | | |
|---|---|---|
| AU | 2002241673 | 11/2005 |
| CA | 2404459 | 8/2005 |

(Continued)

OTHER PUBLICATIONS

Araki, Tohru, et. al., "The Loop-Loosening Procedure for Urination Difficulties After Stamey Suspension of the Vesical Neck," J. of Urology, vol. 144, Aug. 1990, pp. 319-323.

(Continued)

*Primary Examiner* — Navin Natnithithadha
*Assistant Examiner* — Sunita Reddy
(74) *Attorney, Agent, or Firm* — Brake Hughes Bellermann LLP (57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to supportive tissue and adjusting the implant.

22 Claims, 3 Drawing Sheets

(56) References Cited

U.S. PATENT DOCUMENTS

| | | | |
|---|---|---|---|
| 5,362,294 A | 11/1994 | Seitzinger | |
| 5,386,836 A | 2/1995 | Biswas | |
| 5,413,598 A | 5/1995 | Moreland | |
| 5,474,518 A | 12/1995 | Velaquez | |
| 5,611,515 A | 3/1997 | Benderev et al. | |
| 5,628,756 A | 5/1997 | Barker, Jr. et al. | |
| 5,840,011 A | 11/1998 | Landgrebe et al. | |
| 5,842,478 A | 12/1998 | Benderev et al. | |
| 5,860,425 A | 1/1999 | Benderev et al. | |
| 5,899,909 A | 5/1999 | Claren et al. | |
| 5,919,232 A | 7/1999 | Chaffringeon et al. | |
| 5,922,026 A | 7/1999 | Chin | |
| 5,934,283 A | 8/1999 | Willem et al. | |
| 6,010,447 A | 1/2000 | Kardjian | |
| 6,039,686 A | 3/2000 | Kovac | |
| 6,042,534 A | 3/2000 | Gellman et al. | |
| 6,042,536 A | 3/2000 | Tihon et al. | |
| 6,056,688 A | 5/2000 | Benderev et al. | |
| 6,068,591 A | 5/2000 | Bruckner et al. | |
| 6,077,216 A | 6/2000 | Benderev et al. | |
| 6,110,101 A | 8/2000 | Tihon et al. | |
| 6,117,067 A | 9/2000 | Gil-Vernet | |
| 6,221,005 B1 | 4/2001 | Bruckner et al. | |
| 6,302,840 B1 | 10/2001 | Benderev | |
| 6,306,079 B1 | 10/2001 | Trabucco | |
| 6,334,446 B1 | 1/2002 | Beyar | |
| 6,352,553 B1 | 3/2002 | van de Burg et al. | |
| 6,382,214 B1 | 5/2002 | Raz et al. | |
| 6,478,727 B2 | 11/2002 | Scetbon | |
| 6,482,214 B1 | 11/2002 | Sidor, Jr. et al. | |
| 6,575,897 B1 | 6/2003 | Ory | |
| 6,592,515 B2 | 7/2003 | Thierfelder | |
| 6,592,610 B2 | 7/2003 | Beyar | |
| 6,596,001 B2 | 7/2003 | Stormby et al. | |
| 6,599,323 B2 | 7/2003 | Melican et al. | |
| 6,612,977 B2 | 9/2003 | Staskin | |
| 6,638,210 B2 | 10/2003 | Berger | |
| 6,638,211 B2 | 10/2003 | Suslian et al. | |
| 6,638,284 B1 | 10/2003 | Rousseau et al. | |
| 6,641,524 B2 | 11/2003 | Kovac | |
| 6,641,525 B2 | 11/2003 | Rocheleau | |
| 6,648,921 B2 | 11/2003 | Anderson | |
| 6,652,450 B2 | 11/2003 | Neisz et al. | |
| 6,673,010 B2 | 1/2004 | Skiba et al. | |
| 6,685,629 B2 | 2/2004 | Therin | |
| 6,702,827 B1 | 3/2004 | Lund | |
| 6,752,814 B2 | 6/2004 | Gellman et al. | |
| 6,755,781 B2 | 6/2004 | Gellman | |
| 6,802,807 B2 | 10/2004 | Anderson | |
| 6,830,052 B2 | 12/2004 | Carter et al. | |
| 6,881,184 B2 | 4/2005 | Zappala | |
| 6,884,212 B2 | 4/2005 | Thierfelder et al. | |
| 6,908,425 B2 | 6/2005 | Luscombe | |
| 6,911,002 B2 * | 6/2005 | Fierro | A61F 2/0045 600/30 |
| 6,911,003 B2 | 6/2005 | Anderson et al. | |
| 6,953,428 B2 | 10/2005 | Gellman et al. | |
| 6,960,160 B2 | 11/2005 | Browning | |
| 6,971,986 B2 | 12/2005 | Staskin et al. | |
| 6,981,944 B2 | 1/2006 | Jamiolkowski | |
| 7,025,063 B2 | 4/2006 | Snitkin | |
| 7,070,556 B2 | 7/2006 | Anderson | |
| 7,070,558 B2 | 7/2006 | Gellman et al. | |
| 7,083,568 B2 | 8/2006 | Neisz et al. | |
| 7,083,637 B1 | 8/2006 | Tannhauser | |
| 7,087,065 B2 | 8/2006 | Ulmsten et al. | |
| 7,121,997 B2 | 10/2006 | Kammerer et al. | |
| 7,131,944 B2 | 11/2006 | Jaquetin | |
| 7,226,407 B2 | 6/2007 | Kammerer | |
| 7,229,404 B2 | 6/2007 | Bouffier | |
| 7,229,453 B2 | 6/2007 | Anderson | |
| 7,235,043 B2 | 6/2007 | Gellman et al. | |
| 7,261,723 B2 | 8/2007 | Smith et al. | |
| 7,297,102 B2 | 11/2007 | Smith et al. | |
| 7,303,525 B2 | 12/2007 | Watschke et al. | |
| 7,351,197 B2 | 4/2008 | Montpetit et al. | |
| 7,364,541 B2 | 4/2008 | Chu et al. | |
| 7,407,480 B2 | 8/2008 | Staskin et al. | |
| 7,422,557 B2 | 9/2008 | Arnal et al. | |
| 7,500,945 B2 | 3/2009 | Cox et al. | |
| 7,513,865 B2 | 4/2009 | Bourne et al. | |
| 7,527,588 B2 | 5/2009 | Zaddem et al. | |
| 7,601,118 B2 | 10/2009 | Smith et al. | |
| 7,611,454 B2 | 11/2009 | De Leval | |
| 7,621,864 B2 | 11/2009 | Suslian et al. | |
| 7,686,759 B2 | 3/2010 | Sater | |
| 7,740,576 B2 | 6/2010 | Hodroff et al. | |
| 7,762,942 B2 | 7/2010 | Neisz et al. | |
| 7,766,926 B2 | 8/2010 | Bosley et al. | |
| 7,789,821 B2 | 9/2010 | Browning | |
| 7,927,342 B2 | 4/2011 | Rioux | |
| 7,981,024 B2 | 7/2011 | Levy | |
| 2001/0049467 A1 | 12/2001 | Lehe et al. | |
| 2002/0128670 A1 | 9/2002 | Ulmsten et al. | |
| 2002/0147382 A1* | 10/2002 | Neisz | A61B 17/0401 600/29 |
| 2002/0151909 A1 | 10/2002 | Gellman et al. | |
| 2002/0161382 A1 | 10/2002 | Neisz | |
| 2003/0004581 A1 | 1/2003 | Rousseau | |
| 2003/0010929 A1 | 1/2003 | Prieve et al. | |
| 2003/0036676 A1 | 2/2003 | Scetbon | |
| 2003/0065402 A1 | 4/2003 | Anderson et al. | |
| 2003/0176875 A1 | 9/2003 | Anderson | |
| 2004/0015057 A1 | 1/2004 | Rocheleau et al. | |
| 2004/0073235 A1 | 4/2004 | Lund | |
| 2004/0144395 A1* | 7/2004 | Evans | A61B 17/06066 128/885 |
| 2004/0225181 A1 | 11/2004 | Chu et al. | |
| 2004/0231678 A1* | 11/2004 | Fierro | A61B 17/06109 128/885 |
| 2005/0000523 A1 | 1/2005 | Beraud | |
| 2005/0004427 A1 | 1/2005 | Cervigni | |
| 2005/0038451 A1 | 2/2005 | Rao et al. | |
| 2005/0131391 A1 | 6/2005 | Chu et al. | |
| 2005/0131393 A1 | 6/2005 | Chu et al. | |
| 2005/0277806 A1 | 12/2005 | Cristalli | |
| 2005/0283189 A1 | 12/2005 | Rosenblatt et al. | |
| 2006/0058578 A1 | 3/2006 | Browning | |
| 2006/0089524 A1 | 4/2006 | Chu | |
| 2006/0089525 A1* | 4/2006 | Mamo | A61B 17/0401 600/37 |
| 2006/0195007 A1 | 8/2006 | Anderson | |
| 2006/0195010 A1 | 8/2006 | Arnal et al. | |
| 2006/0195011 A1* | 8/2006 | Arnal | A61B 17/06066 600/37 |
| 2006/0217589 A1 | 9/2006 | Wan et al. | |
| 2006/0229493 A1 | 10/2006 | Weiser et al. | |
| 2006/0229596 A1* | 10/2006 | Weiser | A61B 17/00234 606/37 |
| 2006/0252980 A1 | 11/2006 | Arnal et al. | |
| 2006/0287571 A1 | 12/2006 | Gozzi | |
| 2007/0078295 A1* | 4/2007 | Landgrebe | A61B 17/0401 600/37 |
| 2008/0004490 A1* | 1/2008 | Bosley, Jr. | A61B 17/06109 600/37 |
| 2008/0039678 A1 | 2/2008 | Montpetit et al. | |
| 2008/0140218 A1 | 6/2008 | Staskin et al. | |
| 2008/0207989 A1* | 8/2008 | Kaleta | A61B 17/06109 600/37 |
| 2008/0300607 A1 | 12/2008 | Meade et al. | |
| 2009/0221868 A1* | 9/2009 | Evans | A61F 2/0045 600/37 |
| 2010/0256442 A1 | 10/2010 | Ogdahl et al. | |
| 2010/0261950 A1* | 10/2010 | Lund | A61F 2/0045 600/30 |
| 2011/0034759 A1 | 2/2011 | Ogdahl et al. | |
| 2011/0124954 A1 | 5/2011 | Ogdahl | |

(56) References Cited

U.S. PATENT DOCUMENTS

| | | | | |
|---|---|---|---|---|
| 2011/0288368 | A1* | 11/2011 | VanDeWeghe | A61B 17/06109 600/30 |
| 2012/0109195 | A1* | 5/2012 | Odermatt | A61B 17/06166 606/232 |

FOREIGN PATENT DOCUMENTS

| | | |
|---|---|---|
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 1093758 A1 | 4/2001 |
| EP | 1060714 A3 | 9/2002 |
| EP | 1342450 B1 | 9/2003 |
| FR | 2787990 A1 | 7/2000 |
| GB | 2268690 A | 1/1994 |
| GB | 2353220 A | 10/2000 |
| WO | WO9317635 A1 | 9/1993 |
| WO | WO9319678 A2 | 10/1993 |
| WO | WO9819606 A1 | 5/1998 |
| WO | WO9835616 A1 | 8/1998 |
| WO | WO9835632 A1 | 8/1998 |
| WO | WO0018319 A1 | 4/2000 |
| WO | WO0027304 A1 | 5/2000 |
| WO | WO0057812 A1 | 10/2000 |
| WO | WO0066030 A1 | 11/2000 |
| WO | WO0074594 A1 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02089704 A2 | 11/2002 |
| WO | WO03003778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03075792 A1 | 9/2003 |
| WO | WO03092546 A2 | 11/2003 |
| WO | WO2004016196 A2 | 2/2004 |
| WO | WO2004017862 A2 | 3/2004 |
| WO | WO2005037132 A2 | 4/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007/016083 | 2/2007 |
| WO | WO2007014241 A1 | 2/2007 |
| WO | WO2007027592 A2 | 3/2007 |
| WO | WO2007059199 A2 | 5/2007 |
| WO | WO2007097994 | 8/2007 |
| WO | WO2007137226 A2 | 11/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009/075800 | 6/2009 |
| WO | WO2010/028242 | 3/2010 |
| WO | WO2010093421 | 8/2010 |
| WO | WO2011/063412 | 5/2011 |
| WO | WO2011/072148 | 6/2011 |
| WO | WO2011/082350 | 7/2011 |

OTHER PUBLICATIONS

Asmussen et. al., "Simultaneous Urethro-Cystometry with a New Technique," Scand, J. Urol. Nephrol 10:7-11, 1976, pp. 7-10.

Benderev, Theodore, "A Modified Percutaneous Outpatient Bladder Neck Suspension System," The J. of Urology, vol. 152, Dec. 1994, pp. 2316-2320.

Benderev, Theodore, "Anchor Fixation and Other Modifications of Endoscopic Bladder Neck Suspension," Urology, vol. 40, No. 5, Nov. 1992, pp. 409-419.

Blaivas et. al., "Pubovaginal Fascial Sling for the Treatment of Complicated Stress Urinary Incontinence," The J. of Urology, vol. 145, Jun. 1991, pp. 1214-1218.

Burch, John C., "Urethrovaginal fixation to Cooper's ligament for correction of stress incontinence, cystocele, and prolapse," Am. J. Obstetrics and Gynecology, vol. 31, No. 2, Feb. 1961.

Conquy, Dophle, "Le point sur L'incontinence urinaire," Expertise et practiques en urologie, No. 3, 1998.

Das et al., "Laparoscopic colpo-suspension," J. of Urology, vol. 154, pp. 1119-1121, Sep. 1995.

DeLancey, John, "Structural support of the urethra as it relates to stress urinary incontinence: the hammock hypothesis," Am. J. Obstetrics and Gynecology, vol. 170, No. 6, Jun. 1994, pp. 1713-1723.

Enzelsberger et al., "Urodynamic and radiologic parameters before and after loop surgery for recurrent urinary stress incontinence," Acta. Obstet. Gynecol. Scand., 1990; 69:51-54.

Falconer et al., "Clinical outcome and changes in connective tissue metabolism after intravaginal slingplasty in stress incontinent women," Int. Urogynecol. J. (1996) 7:133-137.

Gilja et al., "A modifies raz bladder neck suspension operation (transvaginal burch)," The J. of Urology, vol. 153, 1455-1457, May 1995.

Gittes et al., "No-incision pubovaginal suspension for stress incontinence," The J. of Urology, vol. 138 (1987), pp. 568-570.

Hamilton et al., "Procedures for urinary incontinence in the United States, 1979-1997," Am. J. Obstet. Gynecol. vol. 189, No. 1, pp. 70-75 2003.

Henriksson et al., "A urodynamic evaluation of the effects of abdominal urethrocystopexy and vaginal sling urethroplasty in women with stress incontinence," Am. J. Obstet. Gynecol., vol. 131, No. 1, pp. 77-83, May 1978.

Hodgkinson et al., "Urinary stress incontinence in the female: III. Round-ligament technic for retropubic suspension of the urethra," Obstetrics & Gynecology, vol. 10, No. 5 (1957).

Holschneider et al., "The modified pereyra procedure in recurrent stress urinary incontinence: a 15 year review," Obstetrics & Gynecology, vol. 83, No. 4 pp. 573-579 (1994).

Ingelman-Sundberg, "Surgical treatment of female urinary stress incontinence," Contr. Gynec. Obstet., vol. 10 pp. 51-69 (1983).

Klutke et al., "The anatomy of stress incontinence: magnetic resonance imaging of the female bladder neck and urethra," The J. or Urology, vol. 149, pp. 563-567 (1990).

Klutke et al., "Instruments & Methods: transvaginal bladder neck suspension to cooper's ligament: a modified pereyra procedure," Obstetrics & Gynecology, vol. 88, No. 2, pp. 293-297 (1996).

Leach et al., "Female stress urinary incontinence clinical guidelines panel summary report on surgical management of female stress urinary incontinence," Am. Urological Assc., vol. 158, 875-880 (1997).

Loughlin et al., "Review of an 8-year experience with modifications of endoscopic suspension of the bladder neck for female stress urinary incontinence," The Journal of Urology, vol. 143, pp. 3-4 (1990).

McGuire, Edward, "Abdominal procedure for stress incontinence," Urologic Clinics of North America, vol. 12 No. 5, pp. 285-291 (1985).

(56) References Cited

OTHER PUBLICATIONS

McKiel et al., "Marshall-Marchetti procedure: modifications," The Journal of Urology, vol. 96 (1966).

O'Donnell, Pat, "Combined Raz urethral suspension and McGuire pubovaginal sling for treatment of complicated stress urinary incontinence," The J. of the Ark. Med. Society, vol. 88, No. 8, pp. 389-392 (1992).

Parra et al., "Experience with a simplified technique for the treatment of female stress urinary incontinence," British J. of Urology, vol. 68:615-617 (1990).

Pereyra, Armand, "A simplified surgical procedure for the correction of stress incontinence in women," West. J. Obst. & Gynec., Jul./Aug. 1959.

Pereyra, Armand, "Pubourethral supports in perspective: modified pereyra procedure of urinary incontinence," Obstet. & Gyne. vol. 59. No. 5 (1992).

Petros et al., "The autogenic ligament procedure: a technique for planned formation of an artificial neo-ligament," Acta Obstet Gynecol Scand, 69 Suppl. 153:43-51 (1990).

Petros et al., "Cough transmission ratio: an indicator of suburethral vaginal wall tension rather than urethral closure?", Acta Obstet Gynecol Scand, 69 Suppl. 153:43-51 (1990).

Petros et al., "Non stress non urge female urinary incontinence—diagnosis and cure: a preliminary report," Acta Obstet Gynecol Scand, 69 Suppl. 153:69-70 (1990).

Petros et al., "The role of a lax posterior vaginal fornix in the causation of stress and urgency symptoms: a preliminary report," Acta Obstet Gynecol Scand, 69 Suppl. 153:71-73 (1990).

Petros et al., "The tethered vagina syndrome, post surgical incontinence and I-plasty operation for sure," Acta Obstet Gynecol Scand, 69 Suppl. 153:63-67 (1990).

Petros et al., "Bladder instability in women: a premature activation of the micturition reflex," Neurourology and Urodynamics, 12:235-239 (1993).

Petros et al., "Urethral pressure increase on effort originates from within the urethra, and continence from musculovaginal closure," Neurourology and Urodynamics, 14:337-350 (1995).

Petros et al., "An analysis of rapid pad testing and the history for the diagnosis of stress incontinence," Ada Obstet Gynecol Scand, 71:529-536 (1992).

Petros et al., "An integral theory of female urinary incontinence," Acta Obstet Gynecol Scand, 69 Suppl. 153:7-31 (1990).

Petros et al., "The tuck procedure: a simplified vaginal repair for treatment of female urinary incontinence," Acta Obstet Gynecol Scand, 69 Suppl. 153:41-42 (1990).

Petros et al., "Anchoring the midurethra restores bladder-neck anatomy and continence," The Lancet, vol. 354 (1999).

Petros et al., "The development of the intravaginal slingplasty procedure: IVS II (with bilateral tucks)," Scand. J. Urol. Nephrol. Suppl. No. 153:61-69 (1993).

Petros et al., "Part IV: Surgical applications of the theory—Development of the intravaginal sling plasty (IVS) procedure," Scand. J. Urol. Nephrol. Suppl. No. 153:53-57 (1993).

Petros et al., "An anatomical basis for success and failure of female incontinence surgery," Scand. J. Urol. Nephrol. Suppl. No. 153:55-61 (1993).

Petros et al., "Part II. The biomechanics of vaginal tissue and supporting ligaments with special relevance to the pathogenesis of female urinary incontinence," Scand. J. Urol. Nephrol. Suppl. No. 153:29-31 (1993).

Petros et al., "Further development of the intravaginal slingplasty procedure—IVS III (with midline tuck)," Scand. J. Urol. Nephrol. Suppl. No. 153:69-73 (1993).

Petros et al., "Part III. Surgical principles deriving from the theory," Scand. J. Urol. Nephrol. Suppl. No. 153:41-53 (1993).

Petros et al., "Part I. Theoretical, morphological, radiological correlations and clinical perspective," Scand. J. Urol. Nephrol. Suppl. No. 153:5-29 (1993).

Raz et al., "The Raz bladder neck suspension: results in 206 patients," The Journal of Urology, pp. 845-846 (1992).

Raz et al., "Modified bladder neck suspension for female stress incontinence," Urology, vol. XVII, No. 1, pp. 82-86 (1981).

Richardson et al., "Delayed reaction to the Dacron buttress used in urethropexy," vol. 29, No. 9, pp. 690-694 (1984).

Roberts, Henry, "Cystourethrography in Women," Cystourethrography in Women, vol. XXV No. 293, pp. 253-260 (1952).

Seim et al., "A study of female urinary incontinence in general practice," Scand. J. Urol. Nephrol 30;465-471 (1996).

Sloan et al., "Stress incontinence of urine: a retrospective study of the complications and late results of simple suprapubic suburethral fascial slings," The Journal of Urology, vol. 110, pp. 533-537 (1953).

Spencer et al., "A comparison of endoscopic suspension of the vesical neck with suprapubic vesicourethropexy for treatment of stress urinary incontinence," The Journal of Urology, vol. 137, pp. 411-416 (1987).

Stamey, Thomas, "Endoscopic suspension of the vesical neck for urinary incontinence in females," Am. Surg. pp. 465-472 (1980).

Stanton, Stuart, "Suprapubic approaches for stress incontinence in women," JAGS 38;348-351 (1990).

Studdiford, William, "Transplantation of abdominal fascia for the relief of urinary stress incontinence," Am. J. Obst & Gyne. vol. 47, pp. 764-776 (1994).

Tyco Heathcare, "IVS Tunneller," ICS/IUGA Symp. (2002).

Tyco Heathcare, "IVS Tunneller," ICS/IUGA Symp. (2001).

Ulmsten et al., "The unstable female urethra," Am. J. Obstet & Gynecol. vol. 144, No. 1 (1982).

Ulmsten et al., "Different biochemical composition of connective tissue in continent and stress incontinent women," Acta Obstet. Gynecol. Scand. 66:455-457 (1987).

Ulmsten et al., "Female urinary incontinence—a symptom, not a urodynamic disease. Some theoretical and practical aspect of the diagnosis a treatment of female urinary incontinence," Int. Urogynecology J. 6:2-3 (1995).

Ulmsten et al., "An ambulatory surgical procedure under local anesthesia for treatment of female urinary incontinence," Int. Urogynecology J. 7:81-86 (1996).

Ulmsten et al., "A multicenter study of tension-free vaginal tape (TVT) for surgical treatment of stress urinary incontinence," Int. Urogynecology J. 9:210-213 (1998).

Ulmsten et al., "A three-year follow up of tension free vaginal tape for surgical treatment of female stress urinary incontinence," British Journal of Obstetrics and Gynaecology, vol. 106 pp. 345-350 (1999).

Waxman et al., "Advanced urologic surgery for urinary incontinence," The female Patient, vol. 21, pp. 93-101 (1996).

Webster et al., "Voiding dysfunction following cystourethropexy: its evaluation and management," The Journal of Urology vol. 144, pp. 670-674 (1990).

Webster, George, "Female Urinary Incontinence," Urologic Surgery, $3^{rd}$ Ed., pp. 665-680 (1983).

Winter, Chester, "Peripubic urethropexy for urinary stress incontinence in women," Urology, vol. XX No. 4, pp. 408-412 (1982).

Woodside et al., "Suprapubic endoscopic vesical neck suspension for the management of urinary incontinence in myelodysplastic girls," The Journal of Urology vol. 135, pp. 97-101 (1986).

Zacharin, Robert, "The suspensory mechanism of the female urethra," Journal of Anatomy, vol. 97, Part 3, pp. 423-430 (1963).

Zimmern et al., "Four-Corner bladder neck suspension," Vaginal Surgery for the Urologist, vol. 2, No. 1 pp. 29-37 (1994).

\* cited by examiner

IMPLANTS, TOOLS, AND METHODS FOR TREATMENT OF PELVIC CONDITIONS

PRIORITY CLAIM

This application claims the benefit from International No. PCT/US2012/031592, which as granted an International Filing date of Mar. 30, 2012, which in turns claims priority under 35 USC §119(e) from U.S. Provisional Patent Application having Ser. No. 61/469,458 filed Mar. 30, 2011, which applications are incorporated herein by reference in their entireties.

FIELD OF THE INVENTION

The present invention relates generally to surgical methods and apparatus and, more specifically, to a surgically implantable sling having one or more adjustable features for treating incontinence or other pelvic disorders.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

The tension of an implant (i.e., "sling") is typically adjusted during an implantation procedure in a manner to take up slack in the sling and impart desirable and efficacious tension and positioning of the implanted sling and the supported tissue. New and improved methods of intra-operative implant adjusting mechanisms are always desirable. There is a desire to obtain a minimally invasive yet highly effective implantable mesh that can be used to treat incontinence (fecal or urinary), organ prolapse, and other pelvic conditions, with useful adjustability features.

SUMMARY

Devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, and other conditions caused by muscle and ligament weakness, hysterectomies, and the like.

Various surgical implants, tools, and methods that relate to useful or advantageous surgical procedures are described herein. Certain embodiments of method and implants involve an implant that includes an adjusting mechanism to adjust a length of an implant (e.g., a length of an extension portion or other portion or piece of an implant), intra-operatively.

Described devices and methods involve pelvic implants, including surgical implants (also referred to generally herein as "slings") that include a central support portion and two or more end portions extending from the central support portion to sling ends. Herein, the terms "sling," "implant," and "incontinence sling" without further qualification are used interchangeably to include various forms of pelvic implants for supporting different pelvic tissues, and specifically include urethral slings adapted to be placed through a tissue pathway in a male or female patient, disposing the central support portion below the urethra or bladder neck (hereafter collectively referred to as the urethra for convenience) (and above the vaginal wall in a female patient) to alleviate urinary incontinence, and fecal slings adapted to be placed through a tissue pathway disposing the central support portion inferior to the anus, the anal sphincter, or the lower rectum (hereafter collectively referred to as the anus for convenience) to alleviate fecal incontinence.

In accordance with the present description, such slings include features that enhance intra-operative adjustment of the tension applied to the urethra, anus, or other supported tissue, to enhance efficacy of the implant and method of treatment, and for improved patient comfort. Various specific embodiments of the implants and methods are described herein. The various embodiments are applicable to both male and female patients to address issues of incontinence in both, to address issues of prolapse repair in female patients, and to address perineal floor descent and fecal incontinence in both. Also, surgical techniques such as forming suprapubic, retropubic, transobturator, "inside-out," and "outside-in" tissue pathways between two skin incisions, or a tissue pathway formed from a single incision through the vagina or perineal floor (in male or female patients) are also contemplated for placement of a sling.

In various embodiments, sling tension or length of one or two extension portions of an implant can be adjusted by use of flexible strip located at a location of an implant that be accessed intra-operatively. Various flexible strip embodiments can be useful to decrease a length of an implant or extension portion. Optionally, an implant or method can involve the use of an adjusting mechanism at two opposing locations of an implant, each location being accessible through a surgical incision used to place an implant during a surgical implantation procedure. The two opposing adjusting mechanisms, each involving a flexible strip, may be used in a coordinated manner, meaning that the tension or length of both of the two opposing extension portions are adjusted together. Such coordinated adjustment can advantageously allow a surgeon or other user to adjust the placement, length, or tension of an implant in a manner that does not cause a urethra or other tissue to become located at a non-anatomical position relative to a midline of the patient. Stated differently, two opposing extension portions of an implant can be adjusted together to prevent the urethra or other supported tissue from being moved in a left or a right direction within the patient, which will maintain a correct anatomical position of the urethra or other supported tissue, e.g., at a midline of the patient.

In one aspect, the invention relates to a pelvic implant useful to treat a pelvic condition. The implant includes: a tissue support portion piece, a first extension portion piece, and a second extension portion piece; a first adjusting mechanism comprising a first flexible strip forming a first flexible strip loop connecting the first extension portion piece and the tissue support portion piece, wherein the first flexible strip loop can be tightened to reduce a distance between the first extension portion piece and the tissue support portion piece; a second adjusting mechanism comprising a second flexible strip forming a second flexible strip loop connecting the second extension portion piece and the tissue support portion piece, wherein the second flexible strip loop can be tightened to reduce a distance between the second extension portion piece and the tissue support portion piece. Optionally, the implant can include a self-fixating tip at a distal end of the first extension portion piece and a self-fixating tip at a distal end of the second extension portion piece.

In another aspect the invention relates to a method that provides the implant as described, surgically places the implant in a patient to support pelvic tissue, and actuates (e.g., intra-operatively) an adjusting mechanism (optionally two adjusting mechanism), to reduce a size of one or two flexible strip loops.

BRIEF DESCRIPTION OF THE DRAWINGS

All drawings are not to scale.

DETAILED DESCRIPTION

Pelvic floor disorders include urinary and fecal incontinence, prolapse, cystocele, rectocele, enterocele, uterine and vaginal vault prolapse, levator defects, and others, in male and female patients. These disorders typically result from weakness or damage to normal pelvic support systems. Common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures for treating urinary incontinence include surgical methods that place a supportive implant such as a sling to stabilize or support the bladder neck or urethra. Various different supportive implants and sling procedures are known. Slings and methods can differ based on the type of sling material and anchoring methods used, and placement and technique for placing and supporting the sling, including tissue to be supported. In some cases, a sling is placed under the bladder neck and secured via suspension lines to a point of attachment (e.g. bone) through an abdominal or vaginal incision. Other techniques place a supportive portion of a sling below a urethra or bladder neck, and support the sling by placement of ends at or through obturator foramen tissue. Examples of sling procedures are disclosed in U.S. Pat. Nos. 5,112,344; 5,611,515; 5,842,478; 5,860,425; 5,899,909; 6,039,686, 6,042,534 and 6,110,101.

As used herein the terms "anchor," "tissue fastener," and "self-fixating tip," refer interchangeably and non-specifically to any structure that can connect an implant to supportive tissue of a pelvic region. The supportive tissue may preferably be a soft tissue such as a muscle, fascia, ligament, tendon, or the like. The anchor may be any known or future-developed structure useful to connect an implant to such tissue, including but not limited to a clamp, a line, a soft tissue anchor such as a self-fixating tip, and the like.

An implant can include a tissue support portion (or "support portion") that can be used to support a urethra (including a bladder neck), bladder, vagina, levator, rectum, sphincter, or other pelvic tissue. Supporting a "urethra" refers to supporting tissue that includes the urethra (which can refer to the bladder neck), and that can optionally include tissue adjacent to a urethra such as bulbospongiosus muscle, corpus spongiosum, or both. According to specific methods involving treatment of urinary incontinence, a support portion may be placed below bulbospongiosus muscle to support both bulbospongiosus muscle and corpus spongiosum (along with the urethra), or alternately bulbospongiosus muscle may be dissected and a support portion may be placed to contact corpus spongiosum tissue (to support the urethra).

An implant can additionally include one or more extension portion (otherwise known as an "end" portion or "arm") attached or attachable to the tissue support portion. Normally for treating incontinence an implant can include two opposing extension portions. Extension portions are elongate pieces of material (e.g., mesh, molded implant material, line, or biologic material) that extend from the tissue support portion and are connected to the tissue support portion, and are useful to attach to supportive tissue in the pelvic region (e.g., using an anchor such as a self-fixating tip or another form of tissue fastener) to thereby provide support for the tissue support portion and the supported tissue. Generally for treating incontinence, two extension portions can extend from opposite ends of a tissue support portion as elongate "ends," "arms," or "extensions," and may attach to supportive tissue in the pelvic region by extending through a tissue path to an internal anchoring point (see, e.g., Applicant's copending United States Patent Application Publication number US 2010/256442, filed Aug. 8, 2008, by Ogdahl, entitled SURGICAL ARTICLES AND METHODS FOR TREATING PELVIC CONDITIONS, the entirety of which is incorporated herein by reference), or may extend to an external incision, such as through an obturator foramen and through an external incision at a groin or inner thigh (see, e.g., Applicant's copending United States Patent Publication Number US 2006/0287571, the entirety of which is incorporated herein by reference). Also see U.S. Patent Publication number US 2011/0034759 and WO 2010/093421, PCT/US2010/057879, filed Nov. 23, 2010, and PCT/US2010/059739, filed Dec. 9, 2010, the entireties of which are incorporated hereby by reference.

In exemplary uses, each extension portion can extend from the location of attachment with the tissue support portion of the implant, through pelvic tissue, and to a location of supportive tissue within the pelvic region. The supportive tissue can be at an end of a tissue path used to perform a desired implant procedure, such as at a location at or near an end of an extension portion placed according to a single-incision placement procedure by way of a medial (e.g., vaginal or perineal) incision, specifically including tissue of an obturator foramen.

An implant may include portions, pieces, or sections that are synthetic or of biologic material (e.g., porcine, cadaveric, etc.). Extension portions may be, e.g., a synthetic mesh such as a polypropylene mesh, a molded implant material, or the like. The tissue support portion may be synthetic (e.g., a polypropylene mesh or a molded material) or biologic. Examples of implant products that may be similar to those useful according to the present description include those sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Sparc®, Bioarc®, Monarc®, MiniArc®, InVance™, and AdVance™ for treating urinary incontinence.

An example of a particular type of pelvic implant is the type that includes supportive portions including or consisting of a tissue support portion and two extension portions extending from the tissue support portion. An implant that has exactly two extension portions can be of the type useful for treating urinary incontinence. The term "supportive portions" refers to portions of an implant that function to support tissue after the implant has been implanted and specifically includes extension portions, tissue support portions, and an adjusting mechanism (e.g., line) as described herein, and does not include optional or appurtenant features of an implant such as a tissue fastener, self-fixating tip, or other type of connector for attaching the implant to an insertion tool or supportive tissue.

Dimensions of a tissue support portion can be any dimensions useful to support a specific tissue, e.g., urethral or vaginal tissue, for treating a pelvic condition such as incontinence, prolapse, or another pelvic condition. A tissue support portion for use in treating incontinence can be of sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. Exemplary lengths of a tissue support portion can be in the range from 0.5 to 2 inches, such as from 0.75 to 1.5 inches. Exemplary widths of a tissue support portion can be in the range from 0.4 or 0.5 to 4 centimeters, such as from 1 to 2.5 or 3 centimeters.

An implant (e.g., sling) for placement against a corpus spongiosum for treatment of urinary incontinence in a male patient may optionally and preferably include a widened central support to provide increased contact and frictional engagement with the corpus spongiosum. See, for example, Assignee's copending United States Patent Publication Number US 2006/0287571 and U.S. Pat. No. 7,422,557, the entireties of these applications being incorporated herein by reference.

Dimensions of extension portions can allow the extension portion to reach between a tissue support portion placed to support a pelvic tissue such as tissue of a urethra, (at an end of the extension portion connected to the tissue support portion) and a location at which the distal end of the extension portion attaches to supportive tissue at or about the pelvic region, such as an obturator foramen. Exemplary lengths of an extension portion for use in treating incontinence by placing ends of an extension portion at tissue of an obturator foramen, for example, measured between a connection or boundary between the extension portion and the tissue support portion and a distal end of the extension portion, can be, e.g., from 0.5 to 2.5 inches, preferably from 0.5 to 1.5 inches. These or other lengths will be useful for implants designed to treat other conditions.

Implants as described can include a tissue fastener at a distal end or a distal portion of an extension portion, which is the end or portion not attached to a tissue support portion. (The term "distal" as used in this context generally refers to location at an end of an extension portion away from a tissue support portion.) A tissue fastener at a distal end of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical Implants, Tools, and Methods for Treating Pelvic Conditions, filed Jun. 15, 2007; U.S. patent application Ser. No. 12/223,846, filed Aug. 8, 2008; now U.S. Pat. No. 9,144,426, entitled SURGICAL ARTICLES AND METHODS FOR TREATING PELVIC CONDITIONS; U.S. patent application Ser. No. 12/669,099, filed Jan. 14, 2010, now U.S. Pat. No. 8,597,173, entitled PELVIC FLOOR TREATMENTS AND RELATED TOOLS AND IMPLANTS; and WO 2009/075800, the entireties of which are incorporated herein by reference.)

One embodiment of a tissue fastener is a self-fixating tip. A "self-fixating tip" in general can be a structure (sometimes referred to as a soft tissue anchor) connected at a distal end of an extension portion that can be implanted into supportive tissue (e.g., muscle, fascia, ligament, or other soft tissue) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through a medial incision to reach the interior of the pelvic region, e.g., at a location of an obturator foramen or other supportive tissue. The insertion tool may engage the self-fixating tip at an internal channel of the self-fixating tip, at an external location such as at an external surface of the base, at a lateral extension, or otherwise as desired, e.g., in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in supportive tissue. A lateral extension may be moveable or fixed. The size of the self-fixating tip and optional lateral extensions can be useful to penetrate and become anchored into the tissue. Exemplary self-fixating tips are described in Assignee's copending international patent application PCTUS2007/004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective line) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

According to various systems as described, one or more instrument, insertion tool, adjusting tool, or the like, may be incorporated or used with an implant or method as described. Examples of useful tools include those that generally include one or more (stationary or moveable) thin elongate, relatively rigid shaft or needle that extends from a handle. The handle is located at a proximal end of the device and attaches to one end (a proximal end) of a shaft.

According to some embodiments, a distal end of a shaft can be adapted to engage a portion of an implant such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., U.S. patent application Ser. No. 10/834,943 (U.S. Pat. No. 7,500,945), Ser. No. 10/306,179 (U.S. Pat. No. 7,070,556); Ser. No. 11/347,553 (U.S. Pat. No. 7,422,557); Ser. No. 11/398,368 (U.S. Pat. No. 7,740,576); Ser. No. 10/840,646 (U.S. Pat. No. 7,351,197); Ser. No. 10/840,646; PCT application number 2006/028828; PCT application number 2006/0260618; WO 2010/093421, and US Patent Publication No. 2010-0256442 the entireties of these documents being incorporated herein by reference. These and similar tools can be used as presented in the referenced documents, or with modifications to provide features identified in the present description.

An insertion tool can optionally include a mechanism (a "release mechanism") by which a tissue fastener (e.g., a self-fixating tip) can be securely and releasable engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. For example, an internal channel (or external surface) of a self-fixating tip can include an engaging surface designed to engage a mechanism at a distal end of an insertion tool shaft, while the self-fixating tip is placed at, on, or over the distal end. As an example, an internal or external surface of a self-fixating tip can include a depression, ring, edge, or ledge, that can be rounded, angular, etc. A mechanical detent such as a pin, ball, spring, lever, deflector, or other surface or extension located at the distal end of the insertion tool can be moved, deflected, or extended relative to the distal end of the insertion tool to contact the surface of the self-fixating tip to securely and releasably hold the self-fixating tip at the distal end of the insertion tool and selectively prevent removal of the tip from the distal end until removal is desired. The detent (or other surface or mechanism) can be caused to extend (or retract) from the distal end of the insertion tool by actuating a trigger or other mechanism located at the proximal end (e.g., handle or a proximal location of a shaft) of the insertion tool, to secure (or release) the self-fixating tip. Upon placement of the self-fixating tip at a desired location during a surgical implantation procedure, the insertion tool operator can release the self-fixating tip by use of the trigger or other mechanism at the handle to disengage the detent and cause the tip to become loose. The insertion tool can then be removed from the tissue path and the self-fixating tip can remain in a desired implanted location.

One exemplary form of implant useful for treatment of urinary incontinence is a "mini-sling," or "single incision sling," (e.g., as marketed by American Medical Systems under the trade name MINIARC™). These devices and methods can be suitable for treating male or female urinary (or fecal) incontinence by placement of the sling in a therapeutic anatomical location below a patient's urethra (or anus), through a single vaginal or perineal incision, with placement of tissue fasteners at opposing obturator foramen.

An implant as described herein can include one or preferably two adjusting mechanisms. The implant may be formed into three separate pieces of mesh or molded implant material: a center piece or "tissue support portion piece" that includes the tissue support portion and two opposing ends; a first extension portion piece that that includes a proximal end and a distal end, the distal end optionally and preferably including a self-fixating tip; and a second extension portion piece that includes a proximal end and a distal end, the distal end optionally and preferably including a self-fixating tip. According to these multi-piece (e.g., three-piece) embodiments, a first adjusting mechanism includes a flexible strip that extends between and connects the tissue support portion and an extension portion piece. A second adjusting mechanism includes a flexible strip that extends between and connects the tissue support portion and an extension portion piece.

An exemplary flexible strip can be connected securely to one or the other of the tissue support portion piece or the extension portion piece. The exemplary flexible strip can be connected loosely to the other of the tissue support portion piece or the extension portion piece, after which the flexible strip extends back to the piece to which the flexible strip is securely connected, passing adjustably through that piece. The result is a loop formed by the flexible strip between the two pieces of implant: the flexible strip attached to a first piece of a multi-piece implant, extending to a second piece and passing loosely through the second piece, extending back and passing adjustably through the first piece, with a loose end extending away from the implant. The loose end can be pulled to tighten the loop and to cause the two pieces of implant to be pulled together.

A "flexible strip" as a component of an adjusting mechanism can be extended between a proximal end of an extension portion piece and an end of a tissue support portion piece, forming a loop between the two pieces and a loose end extending from the implant, in a manner that allows the loose end to be pulled, e.g., proximally toward a user, to adjust a length of an extension portion of an implant, to consequently achieve a desired tension of the implant and a desired placement of supported tissue. As used herein, a "flexible strip" is relatively flexible elongate body made of any useful material such as a thin polymeric (e.g., polyolefin such as polypropylene) film. Examples of structures useful as a "flexible strip" include any flexible, flat, and elongate structure in the form of a strip, elongate film, ribbon, or the like, that can function as a flexible strip as described herein.

In certain embodiments, a flexible strip can be used to directly affect a length of an extension portion, such as by reducing a distance between an extension portion piece and a support portion piece of the implant. The flexible strip can be securely connected to an end of a first piece of implant, either an end of the extension portion piece or end of the support portion piece. The flexible strip extends from that secure connection with the first piece, to the second (other) piece (the piece to which the flexible strip is not securely connected), and passes through an aperture in the second piece to produce a moveable engagement with the second piece. From that aperture in the second piece the flexible strip extends back to the first piece and through an aperture in the first piece, to produce another moveable engagement, this one between the flexible strip and the first piece.

An aperture in a piece of implant can be an opening such as a slot or channel extending in a width direction and located at or near an end of the piece of implant. An aperture can be sized and shaped to allow the flexible strip to be loosely threaded through the aperture. The aperture can be sufficiently rigid to maintain its shape when the flexible strip is passed through the aperture, and maintained in tension. For example, a slot-shaped aperture can include reinforced or molded surfaces that are of somewhat more rigidity than a mesh implant material.

Optionally, a flexible strip can include frictional features that engage an aperture, aperture surface, or reinforced aperture surface, to prevent movement of a flexible strip in a direction that would loosen (e.g., enlarge) the loop and increase a length of an extension portion or implant, especially when the flexible strip is under tension. A preferred flexible strip can include multiple frictional extensions that, when the flexible strip is passed through an aperture, optionally under tension, optionally with bending of the flexible strip around an aperture surface, will engage a surface of the aperture and prevent the flexible strip from moving relative to the aperture in a direction that would cause a length of the implant or an extension portion to increase.

The frictional feature can be a surface that extends from a surface or edge of the flexible strip, at a central or edge region relative to a width. The frictional feature may extend from the flexible strip independent of the orientation of the flexible strip, meaning that the frictional feature extends from the flexible strip while the flexible strip is in a flat orientation, as well as when the flexible strip is bent, twisted, or otherwise shaped in a non-flat form. Exemplary such frictional features can include teeth, ridges, extensions, bumps, lumps, buldges, protrusions, detents, springs, etc., formed integrally of the flexible strip material or attached to the flexible strip material, that are of any shape, form, or frictionally-effective size (e.g. at least a visible scale), including rounded, pyramidal, ridged (e.g., repeating triangular or rounded structures extending across a width direction of a flexible strip), and may be stationary or deflectable with a bias to extend away from a surface or base of the frictional strip.

Alternate frictional features may lie flat when a flexible strip is in a flat orientation, and may become extended from the flexible strip upon bending of the flexible strip. For example, such a frictional feature may be formed as a cutout that is attached to the flexible strip at an attached (uncut) end and that includes an extending end (at the cut) that extends away from the flexible strip surface upon bending of the flexible strip.

Other forms of frictional surfaces may be apertures in the flexible strip that frictionally interact with an extended surface located at a surface of the aperture, which surface of the aperture can be in the form of an extension that is a rounded, pyramidal, triangular (ridges), or similar surface extending from a surface of the aperture. The surface of the aperture may be solid or deflectable with a bias to extend away from a surface or base of the aperture.

An adjusting mechanism can also include at least one tether that extends from the implant away from the implant, e.g., in a proximal direction during implantation. The tether may be an extension of the flexible strip (connected to or integral with the flexible strip) extending a distance away from a location at which the flexible strip passes through an aperture at an extension portion piece or a tissue support portion piece. The tether can extend from the implant a sufficient distance to allow the tether to be manipulated manually by a surgeon to pull the tether and tighten the flexible strip during a surgical implantation procedure, through an incision in the patient, without the need for a surgical instrument. In use, traction placed on the tether, such as by pulling in a proximal direction, places traction on the flexible strip, e.g., at the loop formed between the two implant pieces. For example, traction placed on the tether can cause the loop to be reduced in size to bring the pieces of the implant closer together. A preferred tether can include a loose tether end that can be located a distance away from the implant to allow the loose tether end to be manipulated intra-operatively, during a surgical procedure, through a medial incision. With the implant placed to support a pelvic tissue and with two tissue fasteners placed at supportive tissue such as at opposing obturator foramen, the tether can be pulled (e.g., proximally) to manually reduce the size of the loop and adjust the size of the implant or extension portion, without the need for a specialized tool to directly engage the adjusting mechanism intra-operatively.

The flexible strip works in conjunction with the first and second apertures. In use, the flexible strip can be pulled (optionally released) in a manner to adjust tension created in the implant upon placing the tissue support portion piece to support pelvic tissue (e.g., a urethra). The size of the loop of the flexible strip can be reduced to reduce the length of an implant or extension portion, to increase tension in the implant and extension portion and desirably position the supported tissue. When desired length, tension, and positioning are achieved, friction between the flexible strip and at least one of the first and second apertures secures the achieved length, tension, and positioning, and hold the length, tension, and position, post-operatively.

Figure 1:
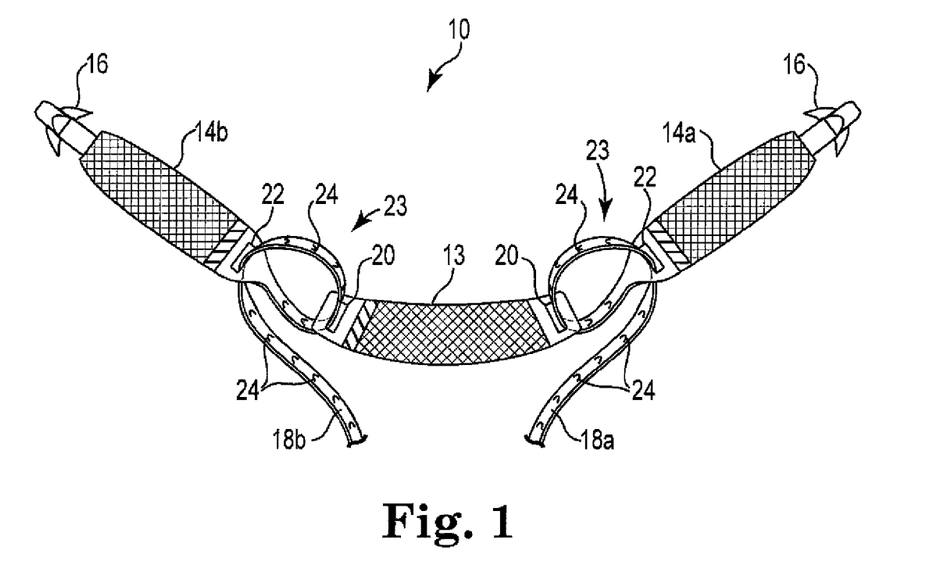
FIG. 1 shows a top perspective view of an example of an implant as described.
Figure 3:
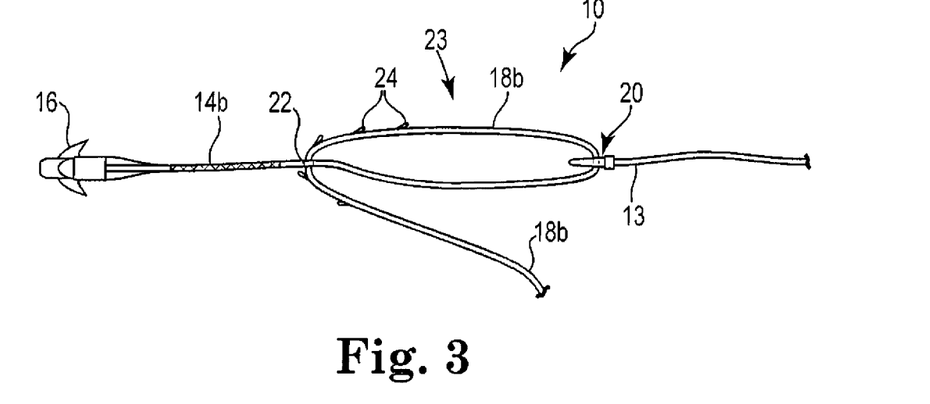
FIG. 3 shows a side view of an example of an implant as described.

Referring to FIG. 1, an exemplary embodiment of an elongated sling 10 is depicted in which features of the present description, including adjusting mechanisms including a flexible strip and a first aperture and a second aperture, are included. Sling 10 includes three implant pieces (e.g., of mesh or molded materials): extension portion piece 14A, extension portion piece 14B, and tissue support portion piece 13. Each extension portion piece 14A and 14B includes a distal end that includes a self-fixating tip 16, which is optional. A proximal end of each extension portion piece 14A and 14B includes aperture 22. Each of two ends of tissue support portion piece 13 includes aperture 20. In an assembled form, flexible strip 18A, 18B is attached at one end to a proximal end of an extension portion piece 14A, 14B, and extends toward tissue support portion piece 13, passing loosely (absent tension) through aperture 20, then extends back toward extension portion piece 14A, 14B to pass through aperture 22, finally extending a length away from implant 10, e.g., in a proximal direction toward a user (e.g., surgeon) when implant 10 is placed therapeutically. Loop 23 is formed between extension portion piece 14A, 14B, by the length of flexible strip 18A, 18B passing from extension portion piece 14A, 14B, to tissue support portion piece 13 and through aperture 20, then back and through aperture 22 of extension portion piece 14A, 14B. FIG. 3 is a side view.

Implant 10 may be implanted by use of any useful method and pathways through which at least extension portions of sling 10 are drawn to dispose support portion piece 13 in operative relation to supported pelvic tissue, such as a urethra or bladder neck (or other pelvic tissue such as an anal sphincter). Sling 10 includes two opposing extension portions (which include but are not necessarily defined by or coextensive with extension portion pieces 14A and 14B), one or more optional tissue fastener 16 located at one or more distal end of the extension portions, and a tissue support portion that is part of (but not necessarily coextensive with) tissue support portion piece 13. Two flexible strips 18A and 18B, forming loops 23, are located on two opposing sides of tissue support portion piece 13. Each flexible strip 18A, 18B connects one end of tissue support portion piece 13 to a proximal end of extension portion pieces 14A and 14B, respectively. The depicted exemplary sling 10 thus extends between two opposing extension portion distal ends, each optionally including a self-fixating tip 16. Each extension portion is associated with a flexible strip 18A, 18B, which can be used to intra-operatively reduce a size (length) of an extension portion.

Figure 2:
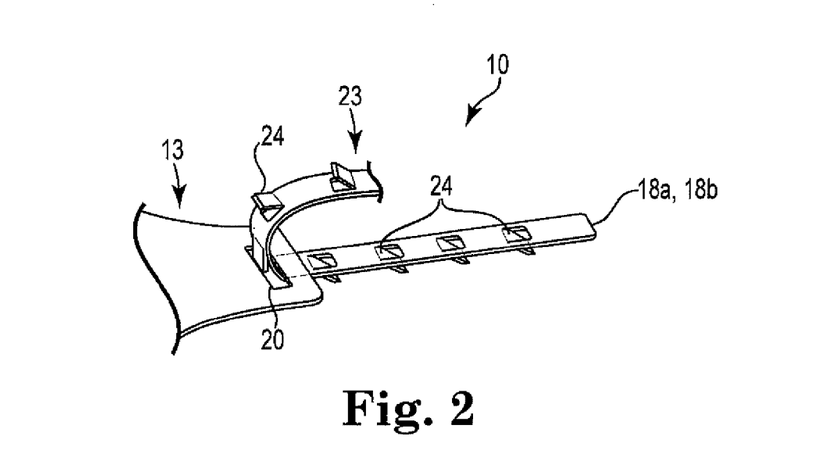
FIG. 2 shows an example of components of an implant as described.

FIG. 2 shows details of flexible strip 18A, 18B, and frictional features 24. Flexible strip 18A, 18B, is illustrated as a flat polymeric strip, such as flexible biocompatible or bioabsorbable polymer such as silicone, polyurethane, polyolefin (e.g., polypropylene), or the like, which can be formed by molding, extrusion, or by cutting (e.g., laser cutting) from a large sheet, then secured to an end of extension portion piece 14A, 14B (e.g., mechanically, by injection molding, by use of an adhesive, etc.) As illustrated, frictional features 24 are formed by making cuts (e.g., by laser cutting) at intervals along a length of flexible strip 18A, 18B. As shown at FIG. 1, the cuts form a corner and a point that extends from flexible strip 18A, 18B; as shown at FIG. 2, the cuts have three lines and two corners, forming a square or rectangular shape that extends from flexible strip 18A, 18B. Other linear, cornered, or curved (e.g., circular) shapes can also be useful. Frictional features 24 may alternately be extensions formed separately and secured to, or alternately integrally molded at, locations along a length of flexible strip 18A, 18B.

Frictional features 24 as illustrated at FIG. 2 are biased to extend away from flexible strip 18A, 18B. When flexible strip 18A, 18B lies flat, frictional features formed by cutting flexible strip 18A, 18B are biased to extend away from the surface of flexible strip 18A, 18B, such as is shown by the flat-lying length of flexible strip 18A, 18B extending away from aperture 20 in a direction toward an extension portion piece (not shown).

Figure 4:
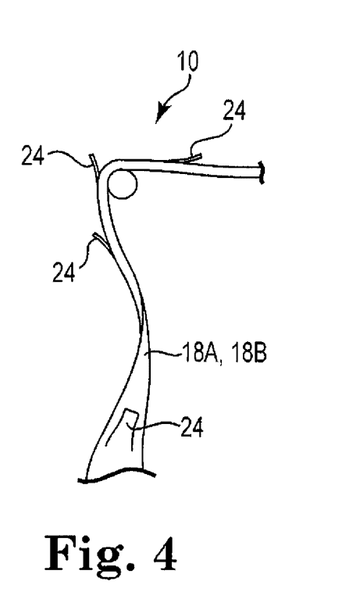
FIGS. 4 and 5 show examples components of implants as described.
Figure 5:
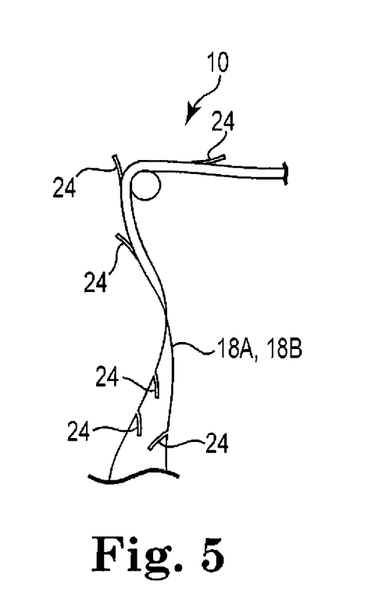

In alternate forms, frictional features 24 can be flat when a flexible strip 18A, 18B lies flat, and can become extended away from the flexible strip 18A, 18B upon bending of the flexible strip. Examples of these types of frictional features are shown at FIGS. 4 and 5. FIG. 4 shows a series of center-cut frictional features that lie flat on a flexible strip 18A, 18B, as the flexible strip lies flat, and become extended from the flexible strip 18A, 18B as the flexible strip becomes bent, e.g. as part of a loop under tension and passing through an aperture of an extension portion piece or a tissue support portion piece. FIG. 5 shows a series of side-cut frictional features that lie flat on a flexible strip 18A, 18B, as the flexible strip lies flat, and become extended from the flexible strip 18A, 18B as the flexible strip becomes bent, e.g. as part of a loop under tension and passing through an aperture of an extension portion piece or a tissue support portion piece.

Figure 6:
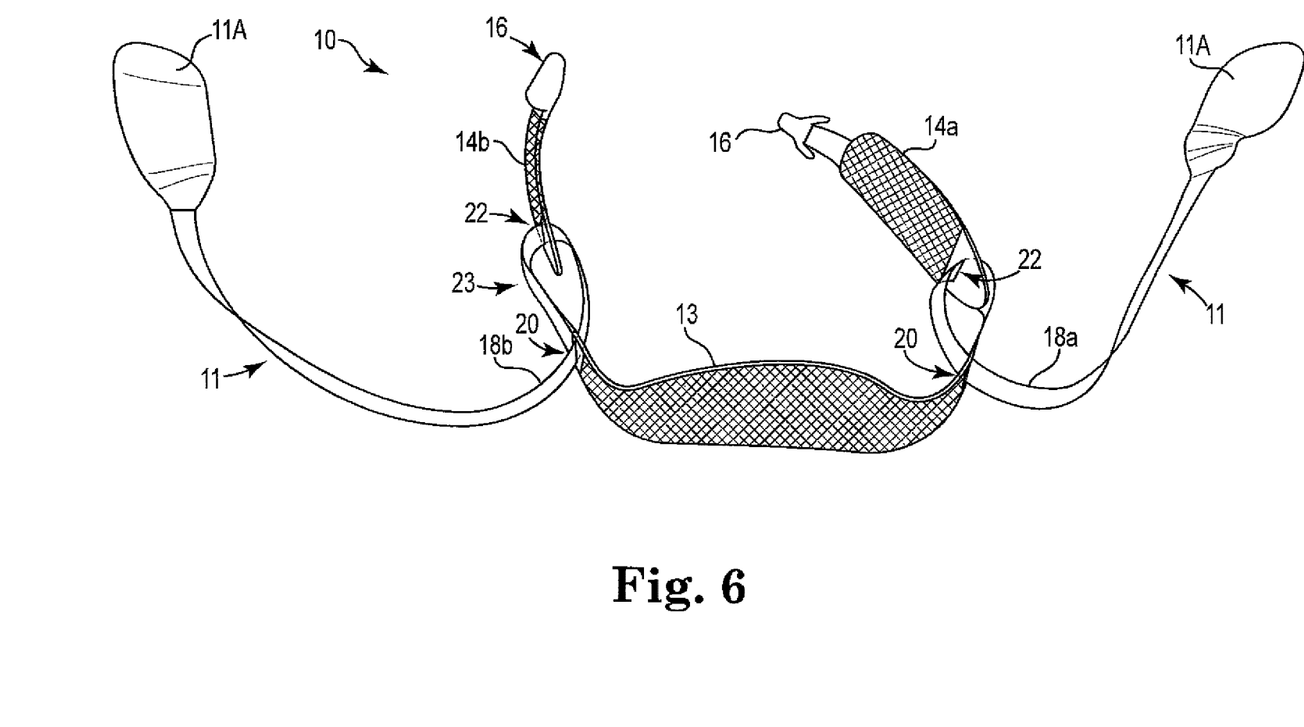
FIG. 6 shows a top perspective view of an example of an implant as described.

FIG. 6 shows an alternate embodiment of an implant 10 as described. Implant 10 of FIG. 6 is similar to that of implant 10 of FIG. 1, but is different in the attachment point of flexible strip 18A, 18B securely to tissue support portion 13, as opposed to being securely attached to extension portion pieces 14A, 14B (at FIG. 1). Implant 10 of FIG. 6 also explicitly illustrates tether 11, which includes tabs 11A.

Referring to implants 10 of the figures, for use as a single-incision sling for treating urinary incontinence, a total length dimension between distal ends of the opposing extension portions (e.g., opposing tissue fasteners 16) can be at least sufficient to extend from an obturator internus muscle on one side of the urethra to an obturator internus muscle on the opposite side of the urethra, with tissue support portion piece 13 placed to support tissue of a urethra. For use in treating urinary incontinence by a single incision method, exemplary dimensions of sling 10 may be 6-15 cm in length (between distal ends), e.g., from 6 to 10 or 8 to 10 centimeters in length, and 1-2 cm, more preferably 1-1.5 cm, in width (at the extension portions). These dimensions are for an implant designed to treat incontinence by a single incision method; dimensions can be substantially different for implants designed to treat a different conditions (e.g., fecal incontinence) or for implantation by a different surgical placement method.

In use, implant 10 is initially placed at a location to support pelvic tissue, with distal ends located at supportive tissue. Each loop 23 of flexible strips 18A and 18B is initially not tensioned. To adjust (reduce) a length of an extension portion, to increase tension of implant 10, and add support to the pelvic tissue, a user can place traction on one or more of a loose end of flexible strips 18A, 18B, e.g., at a tether 11 or a tab 11A, to pull the loose end, tether, or tab in a proximal direction. Preferably, a user can access and manipulate one or more of a flexible strip 18A, 18B, tether 11 or a tab 11A, manually through a surgical (e.g., medial, such as vaginal or perinael) incision, intra-operatively, without the need for a surgical tool or instrument. The size of loop 23 is reduced with tension being applied along the entire length of flexible strip 18A, 18B. Friction between flexible strip 18A, 18B, and apertures 20 and 22, can increase as tension is applied to the implant. Optional frictional features 24 can additionally increase the friction between flexible strip 18A, 18B, and apertures 20 and 22. Friction under tension inhibits or prevents post-operative movement of flexible strip 18A, 18B in a direction that would loosen the tension in implant 10 or allow loops 23 to loosen and slip back to a larger size, which would increase the length of implant 10 or extension portions. Extra lengths of flexible strips 18A, 18B extending away from implant 10 at aperture 20 or 22 can be trimmed upon adjustment.

Optionally and preferably an implant (e.g., any embodiment described herein) can include two adjusting mechanisms (as illustrated to include a flexible strip) at opposing locations of an implant. The two adjusting mechanisms can be actuated (e.g., tightened) in coordination, meaning that the tension or length of both of the two opposing extension portions are adjusted together. Such coordinated use of two adjusting mechanisms can advantageously allow a surgeon or other user to adjust the placement, length, or tension of an implant or extension portion in a manner that does not cause a urethra or other tissue to become located at a non-anatomical position relative to a midline of the patient. Stated differently, two opposing adjusting mechanisms can be actuated and adjusted together to prevent the urethra or other supported tissue from being moved in a left or a right direction within the patient, which will maintain a correct anatomical position of the urethra or other supported tissue, e.g., at a midline of the patient.

Generally, an implant as described can be initially placed with approximate positioning and effect (e.g., supportive force, approximation, tension, etc.) to support selected pelvic tissue. Subsequently, lengths of opposing extension portions can be adjusted by use of the described adjusting mechanisms. Each self-fixating tip 16 can be placed within supportive tissue such as tissues of a patient's two opposing obturator foramen while the tissue support portion of the implant supports a urethra, bladder neck, vaginal tissue, etc.

With reference to a transvaginal method of treating urinary incontinence, exemplary method steps include an initial step of placing implant 10, followed by an adjustment step for adjusting lengths of one or two extension portions, via the described adjusting mechanisms. In a first step, a self-fixating tip 16 can be placed at an end of an insertion tool (optionally including a release mechanism), passed through a medial incision in a patient (e.g., transvaginally), and placed securely into tissue of an obturator foramen. A second self-fixating tip 16 located on the opposite extension portion of implant 10 can be inserted into tissue of the opposite obturator foramen using the same insertion tool or a second identical or similar tool. Optionally, each step of placing a self-fixating tip at tissue of an obturator foramen can include the use of a release mechanism capable of engaging a self-fixating tip 16 at a tip of the insertion tool shaft, placing the self-fixating tip 16 at supportive tissue, releasing self-fixating tip 16 in the supportive tissue, and withdrawing the insertion tool from the patient.

With opposing self-fixating tips installed at opposing obturator foramen, the tissue support portion (of piece 13) is located below a urethra, to support the urethra. The surgeon can assess the position, tension, or both, of implant 10 supporting the urethra, and whether a length of one or two extension portions should be adjusted. Optionally the surgeon may use a "cough test," by asking the patient to cough and checking efficacy of the treatment. If adjustment is necessary, the surgeon can actuate an adjusting mechanism by pulling a flexible strip 18A, 18B, a tether 11, or tab 11A, to reduce a length of an extension portion, i.e., a distance between extension portion piece 14A or 14B and tissue support portion piece 13.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A pelvic implant useful to treat a pelvic condition, the implant comprising:
   a tissue support portion piece, a first extension portion piece, and a second extension portion piece,
   a first adjusting mechanism comprising an elongate first flexible strip having a length, a width, and a thickness, the length being greater than the width, and the width being greater than the thickness, the first flexible strip comprising first edge and second edge opposite the first edge extending in the length and thickness directions and a first surface and an opposed second surface extending in the length and width dimensions between the opposed edges, the first flexible strip forming a first flexible strip loop connecting the first extension portion piece and a first end of the tissue support portion piece, wherein the first flexible strip loop is configured to be tightened to reduce a distance between the first extension portion piece and the tissue support portion piece,
   a second adjusting mechanism comprising a second flexible strip having a length, a width, and a thickness, the length being greater than the width, and the width being greater than the thickness, the second flexible strip comprising a first edge and a second edge opposite the first edge extending in the length and thickness directions and a first surface and an opposed second surface extending in the length and width dimensions between the opposed edges, the second flexible strip forming a second flexible strip loop connecting the second extension portion piece and a second end of the tissue support portion piece, wherein the second flexible strip loop is configured to be tightened to reduce a distance between the second extension portion piece and the tissue support portion piece,
   a self-fixating tip at a distal end of the first extension portion piece, and
   a self-fixating tip at a distal end of the second extension portion piece.

2. The implant as recited at claim 1, wherein
   the tissue support portion piece comprises a first end comprising a first aperture and a second end comprising a second aperture,
   the first extension portion piece comprises an aperture at a proximal end, and the second extension portion piece comprises an aperture at a proximal end.

3. The implant as recited at claim 2, wherein
   an end of the first flexible strip is secured to the first end of the tissue support portion piece,
   the first flexible strip loop extends from the first end of the tissue support portion piece and passes through the aperture at the proximal end of the first extension portion piece, from where the first flexible strip loop then extends to and passes through the aperture at the first end of the tissue support portion piece, the first flexible strip extends away from the aperture at the first end of the tissue support portion piece as a loose end that can be pulled to tighten the first flexible strip loop to reduce a distance between the first extension portion piece and the tissue support portion piece.

4. The implant as recited at claim 3 comprising supportive portions consisting of a central support portion and two extension portions.

5. The implant as recited at claim 2, wherein
an end of the first flexible strip is secured to the proximal end of the first extension portion piece,
the first flexible strip loop extends from the proximal end of the first extension portion piece and passes through the aperture at the first end of the tissue support portion piece, from where the first flexible strip loop then extends to and passes through the aperture at the proximal end of the first extension portion piece,
the first flexible strip extends away from the aperture at the proximal end of the first extension portion piece as a loose end that can be pulled to tighten the first flexible strip loop to reduce a distance between the first extension portion piece and the tissue support portion piece.

6. The implant as recited at claim 5 comprising supportive portions consisting of a central support portion and two extension portions.

7. The implant as recited at claim 5 comprising frictional features located on one of the first or the opposed second surfaces of the first and the second flexible strips.

8. The implant as recited at claim 7, wherein the frictional feature includes teeth, ridges, extensions, bumps, lumps, bulges, protrusion, detents, or springs.

9. The implant as recited at claim 1, wherein the implant has a length to allow the self-fixating tips to be placed at tissue of opposing obturator foramen of a patient, with the tissue support portion supporting tissue of a urethra or anus.

10. The implant as recited at claim 1, wherein the first flexible strip comprises frictional features extending from one of the first and opposed second surfaces.

11. The implant as recited at claim 10, wherein frictional features are formed by making a cut in the first flexible strip, wherein the frictional features lie flat when the flexible strip lies flat, and the frictional features extend from the one of the first and opposed second surfaces of the flexible strip when the flexible strip bends.

12. The implant as recited at claim 11, wherein, when the first flexible strip passes through one of the apertures by bending, the frictional features extend from the one of the first and opposed second surfaces of the first flexible strip and engage a surface of the aperture, preventing movement of the first flexible strip in a manner that would increase the size of the first flexible strip loop.

13. The implant as recited at claim 11, wherein, with the first flexible strip under tension, the frictional feature prevents movement of the first flexible strip in a manner that would increase the size of the first flexible strip loop.

14. The implant as recited at claim 10, wherein the frictional feature is selected from: teeth, ridges, extensions, bumps, lumps, bulges, protrusion, detents, or springs.

15. The implant as recited at claim 1, wherein, with the implant placed within a patient with the self-fixating tips at tissue of opposing obturator foramen and the central support portion supporting tissue of a urethra or anus, a proximal end of the first flexible strip is capable of being accessed through a medial incision of the patient to actuate the first adjusting mechanism.

16. A method of treating a pelvic condition, the method comprising providing an implant as recited at claim 1,
placing the implant in a patient to support pelvic tissue,
actuating the first adjusting mechanism to reduce a size of the first flexible strip loop.

17. The method as recited at claim 16 comprising actuating the second adjusting mechanism to reduce a size of the second flexible strip loop.

18. The method as recited at claim 16, wherein the pelvic condition is selected from the group consisting of: fecal incontinence and urinary incontinence.

19. The method as recited at claim 16 for treating urinary incontinence, the method comprising:
creating a medial incision in the patient,
placing the tissue support portion piece to contact tissue to support a urethra,
placing the distal end of the first extension portion piece in a tissue path extending toward a first obturator foramen of the patient, and
placing the distal end of the second extension portion piece in a tissue path extending toward a second obturator foramen of the patient.

20. The implant as recited at claim 1, wherein the first flexible strip is not a suture and the second flexible strip is not a suture.

21. The implant as recited at claim 1, wherein the first flexible strip has a rectangular cross section when viewed along the length.

22. A pelvic implant useful to treat a pelvic condition, the implant comprising:
a tissue support portion piece, a first extension portion piece, and a second extension portion piece,
a first adjusting mechanism comprising an elongate first flexible strip having a length, a width, and a thickness, the length being greater than the width, and the width being greater than the thickness, the first flexible strip comprising a first edge and a second edge opposite the first edge extending in the length and thickness directions and a first surface, an opposed second surface extending in the length and width dimensions between the opposed edges, the first flexible strip forming a first flexible strip loop connecting the first extension portion piece and a first end of the tissue support portion piece, and frictional features extending from one of the first and opposed second surfaces, wherein the first flexible strip loop is configured to be tightened to reduce a distance between the first extension portion piece and the tissue support portion piece,
a second adjusting mechanism comprising a second flexible strip having a length, a width, and a thickness, the length being greater than the width, and the width being greater than the thickness, the second flexible strip comprising a first edge and a second edge opposite the first edge extending in the length and thickness directions and a first surface and an opposed second surface extending in the length and width dimensions between the opposed edges, the second flexible strip forming a second flexible strip loop connecting the second extension portion piece and a second end of the tissue support portion piece, wherein the second flexible strip loop is configured to be tightened to reduce a distance between the second extension portion piece and the tissue support portion piece, wherein, when the first flexible strip passes through an aperture of the tissue support portion piece, with the first flexible strip under tension, the frictional features extend from one of the first and opposed second surfaces and engage a surface of the aperture, preventing movement of the first flexible strip in a manner that increases the size of the first flexible strip loop, a self-fixating tip at a distal end of the first extension portion piece, and a self-fixating tip at a distal end of the second extension portion piece.

\* \* \* \* \*